(12) United States Patent
Gersh et al.

(10) Patent No.: US 11,291,865 B2
(45) Date of Patent: Apr. 5, 2022

(54) VERIFICATION SYSTEM FOR ROBOTIC RADIOSURGERY

(71) Applicant: Standard Imaging, Inc., Middleton, WI (US)

(72) Inventors: Jacob A. Gersh, Greenville, SC (US); Regina K. Fulkerson, Dundee, NY (US)

(73) Assignee: Standard Imaging, Inc., Middleton, WI (US)

( * ) Notice: Subject to any disclaimer, the term of this patent is extended or adjusted under 35 U.S.C. 154(b) by 498 days.

(21) Appl. No.: 16/182,124

(22) Filed: Nov. 6, 2018

(65) Prior Publication Data

US 2019/0134428 A1   May 9, 2019

Related U.S. Application Data

(60) Provisional application No. 62/582,599, filed on Nov. 7, 2017.

(51) Int. Cl.
*A61N 5/10* (2006.01)
*G01T 1/29* (2006.01)
*A61B 90/00* (2016.01)
*G01T 1/16* (2006.01)

(52) U.S. Cl.
CPC ............ *A61N 5/1083* (2013.01); *A61B 90/39* (2016.02); *A61N 5/1042* (2013.01); *A61N 5/1071* (2013.01); *G01T 1/1603* (2013.01); *G01T 1/29* (2013.01); *G01T 1/2921* (2013.01); *A61B 2090/3966* (2016.02); *A61N 2005/1054* (2013.01); *A61N 2005/1061* (2013.01); *A61N 2005/1074* (2013.01)

(58) Field of Classification Search
CPC .. A61N 5/1083; A61N 5/1042; A61N 5/1071; A61N 2005/1054; A61N 2005/1061; A61N 2005/1074; A61N 5/103; A61N 5/1037; A61B 90/39
See application file for complete search history.

(56) References Cited

U.S. PATENT DOCUMENTS

| | | | |
|---|---|---|---|
| 8,218,725 B2 | 7/2012 | Muller et al. | |
| 2007/0071176 A1* | 3/2007 | Main .................... | A61N 5/1048 378/207 |
| 2018/0028133 A1* | 2/2018 | Jones .................... | G06T 7/0012 |

* cited by examiner

*Primary Examiner* — Samuel G Gilbert
(74) *Attorney, Agent, or Firm* — Boyle Fredrickson, S.C.

(57) ABSTRACT

A verification device for robotic radiotherapy provides beam imaging displaced from an isocenter of a treatment plan to isolate individual beams for comparison to a baseline image to deduce convergence or target deviations in each of three dimensions over the area of a planar imager and perpendicular to that area.

19 Claims, 5 Drawing Sheets

VERIFICATION SYSTEM FOR ROBOTIC RADIOSURGERY

CROSS REFERENCE TO RELATED APPLICATION

This application claims the benefit of U.S. provisional application 62/582,599 filed Nov. 7, 2017, and hereby incorporated by reference in its entirety.

BACKGROUND OF THE INVENTION

The present invention relates generally to medical equipment for therapeutic radiation treatment via a linear accelerator and in particular to a verification system for multi-axis radiotherapy systems, generally termed robotic radiosurgery systems.

Tumors and other medical conditions may be treated by high-energy radiation such as megavoltage radiation collimated and directed through a patient to a point of treatment. When the point of treatment is within the patient, tissue outside of that treatment region along the path of radiation is necessarily subject to radiation. The radiation dose to this surrounding tissue can be reduced by moving the axis of radiation propagation among a variety of angles during treatment. Each of these angles of propagation sequentially expose the treatment site to cumulatively add dose to the treatment site but outside of the treatment site spread the radiation to different tissue reducing the dose to any individual tissue outside of the treatment site.

Providing different angles of radiation propagation may be done, for example, through the use of a rotating gantry changing the angle of radiation propagation within a plane. A more versatile system mounts a lightweight linear accelerator for producing megavoltage radiation on a robotic arm, for example, having six degrees of freedom. This robotic arm may then be readily manipulated to direct the radiation at a variety of angles about the patient in three dimensions.

The robotic arm may also move the radiation source during treatment to follow patient motion (for example, from respiration) or to correct for patient, tumor location and/or tumor size changes, between treatment sessions. For this purpose, fiducial markers may be placed on the patient or near the treatment site (for example, by implanting). These fiducial markers can then be tracked by an auxiliary imaging system to adjust the robotic arm position in real time.

Radiotherapy systems employing robotic arms are desirably subject to regular verification to ensure their correct operation with respect to beam output, beam collimation, and beam positioning. This latter verification of beam positioning can be particularly complex with a robotic arm-type radiotherapy system which can produce a variety of different types of positional error, for example, offsets in each of three dimensions or rotation and the like. As a result regularly verifying such systems can be time-consuming and expensive.

SUMMARY OF THE INVENTION

The present invention provides a verification system for robotic radiotherapy systems that may operate with a planar imaging panel, for example, positioned on the patient table, to quickly identify a variety of positional errors. Fiducial markers affixed to the planar imaging panel allow definition of an alignment localization point and target below the acquisition plane of the planar imaging panel. An isocentric application of beams to the target location produces isolated beam images which may be compared to a similar baseline image to detect position differences between the baseline image and subsequent verification images revealing displacement in any of three dimensions and/or rotation.

Specifically then, the present invention provides a radiotherapy verification system for use with a robotic radiotherapy machine of the type having a treatment head emitting a beam of collimated high-energy radiation and maneuverable by a multi-axis robot arm. The radiotherapy verification system includes a planar imaging device detecting areas of high-energy radiation passing through a plane of the planar imaging device. The planar imaging device communicates with an electronic computer which may receive location information about the areas and execute a stored program held in non-transitory computer readable medium to operate; (a) in a first mode recording location information for the areas during a first execution of a isocentric treatment plan by the robotic radiotherapy machine to provide baseline location information, the isocentric treatment directed to a target region displaced from the plane of the planar imaging device; and (b) in a second mode recording location information for the areas during execution of a second execution of the isocentric treatment plan to provide verification location information and comparing the verification location information to the baseline location information to indicate displacement of the target region between the first execution and second execution.

It is thus a feature of at least one embodiment of the invention to provide a simple verification system for robotic radiotherapy machines that can characterize positional errors using a simple planar imaging device which may be, for example, placed on a patient table.

The second step may further include determining centroids of areas and comparing the verification location information to the baseline location information to compare centroids of the areas.

It is thus a feature of at least one embodiment of the invention to provide high precision machine position data from the beam produced by the treatment head through a statistical combination of data from an exposed area by the beam.

The displacement of the target region may indicate displacement in in three mutually perpendicular directions including displacement above or below the plane of the imaging device.

It is thus a feature of at least one embodiment of the invention to provide multiple dimensions of positional error detection including perpendicular to the plane of the imaging device with a single planar imaging device statically placed during the verification process. By separation of the beams through an out-of-plane target location, convergence of the beams may be deduced by beam separation in a perpendicular plane.

The indication produced by the verification system may provide a distance value equal to the displacement of the target region between the first execution and second execution.

It is thus a feature of at least one embodiment of the invention to provide high-resolution positional error output from measurements of radiation beams.

Alternatively, the indication produced by the verification system may provide pass/fail type output determined by comparing a distance value equal to the displacement of the target region between the first execution and second execution to a predetermined threshold value.

It is thus a feature of at least one embodiment of the invention to permit rapid completion of the verification process with a simple binary output.

The planar imaging device may further include a set of radiopaque fiducial markers affixed at a predetermined location with respect to the planar imaging device.

It is thus a feature of at least one embodiment of the invention to eliminate the need to manually localize and position the planar imaging device by employing the compensation system of the radio therapy machine more typically used for patient motion correction.

The planar imaging device may have an upper surface positionable toward the treatment head and radiopaque fiducial markers positioned beneath a radiation sensor of the planar imaging device to receive radiation passing through the radiation sensor of the planar imaging device and to block a portion of that energy to permit imaging of the fiducial markers through the planar imaging device.

It is thus a feature of at least one embodiment of the invention to permit permanent affixation of the fiducial markers to the detector's radiation-responsive plane for ease of use.

The electronic computer may further record location information for the areas in multiple operations in the second mode linked to time to provide for a history of indications to provide trend information.

It is thus a feature of at least one embodiment of the invention to permit trend analysis that may provide additional information with respect to maintenance of the radiotherapy machine or possible failure modes.

The electronic computer may further operate in the second mode to compare the verification location information to the baseline location information to indicate a rotation of the areas between the first execution and second execution.

It is thus a feature of at least one embodiment of the invention to permit additional dimensions of verification that may be valuable for certain types of radiation delivery systems.

These particular objects and advantages may apply to only some embodiments falling within the claims and thus do not define the scope of the invention.

DETAILED DESCRIPTION OF THE PREFERRED EMBODIMENT

Figure 1:
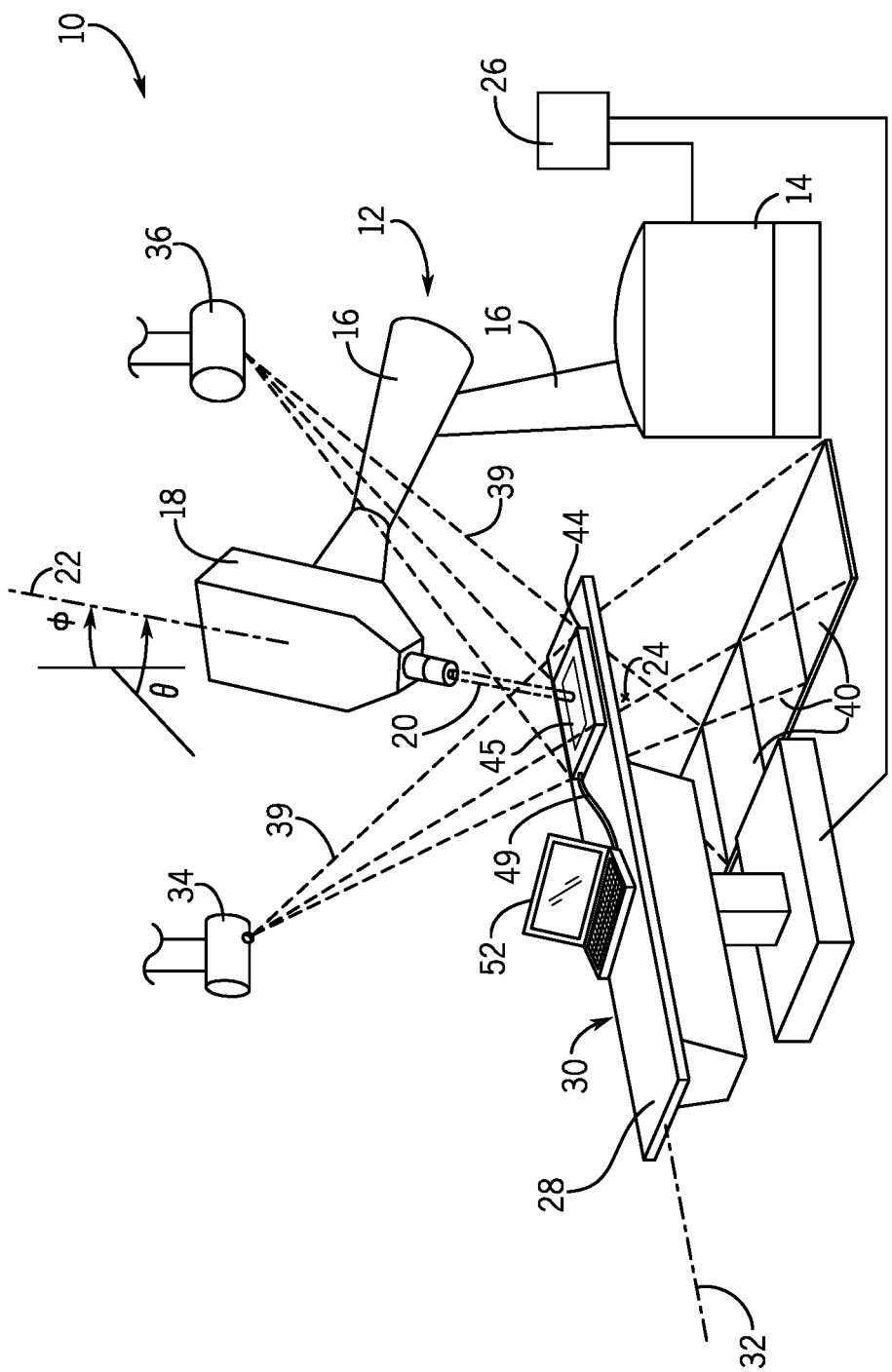
FIG. 1 is a perspective view of a robotic radiation therapy system providing a treatment head for delivering a collimated beam of high energy radiation toward a patient support holding a planar detector communicating with an electronic computer and showing ceiling-mounted kilovoltage x-ray sources producing beams imaging the planar detector in conjunction with floor-mounted image detectors for the imaging of fiducial markers in the planar detector.

Referring now to FIG. 1, a robotic radiation therapy system 10 may include a robot arm 12, for example, supported on a base 14 attached to a floor of an operating room and extending upward through multiple segments 16, each providing a different axis of motion, to attach to a treatment head 18. Generally each of the segments 16 may include a servo motor allowing them to be independently rotated or extended per signals received by a controller 26.

The treatment head 18 provides a source of high-energy radiation, for example, a linear accelerator or radioisotope source (not shown) focused and collimated to direct a high-energy beam 20 out of one end of the treatment head 18 generally along an axis 22.

Operation of the robot arm 12 allows the axis 22 of the treatment head to be moved to various locations allowing isocentric treatment of a baseline target isocenter 24 in which a set of sequentially activated beams 20 converge on the baseline target isocenter 24 at a variety of angles distributed in three dimensions. For example, the multiple beams 20 may be distributed about the baseline target isocenter 24 at different polar angles and azimuthal angles intersecting spaced nodes over the surface of a hemisphere about the baseline target isocenter 24. The baseline target isocenter 24 may be defined freely with control of the robot arm 12 adjusted appropriately.

The robot arm 12 may be positioned near a patient support table 28 providing a horizontal radiolucent support surface 30 for supporting a supine patient (not shown) for treatment. The patient support table 28 may also provide servomotors controllable by the controller 26 to control elevation of the surface 30 above the treatment room floor and translation of the surface 30 along a horizontal axis 32 for locating different portions of the patient with respect to the baseline target isocenter 24. The invention may also work with a patient support table 28 providing yaw or angulation about a vertical axis as well as other angulations.

A first and second x-ray source 34 and 36 positioned on opposite sides of the robot arm 12, supported at the ceiling of the treatment room, may be oriented to project kilovoltage x-ray beams 39 downward through the table 28 near the region of the baseline target isocenter 24 to be received by floor mounted planar detectors 40. During normal use, radio-opaque fiducial markers, typically embedded within tissue to be treated, are imaged at different angles by the combination of the first and second x-ray source 34 and 36 and associated floor mounted planar detectors 40 to provide stereoscopic imaging localizing the fiducials in three dimensions. The controller 26 may be programmed (for example, through an operator terminal not shown) to define the baseline target isocenter 24 with respect to the fiducial markers. In this way, movement of the fiducial markers can reveal movement of the target region to track the desired tissue to be treated, with this movement of the target tissue used to shift a reference frame for the robot arm 12 to preserve isocentric treatment with such patient movement. That is, the baseline target isocenter 24 may dynamically track the desired treatment region of the patient with patient movement.

Robotic radiotherapy systems of this type are commercially available, for example, from Accuray Inc. of Sunnyvale, Calif., USA, under the tradename CyberKnife.

Figure 2:
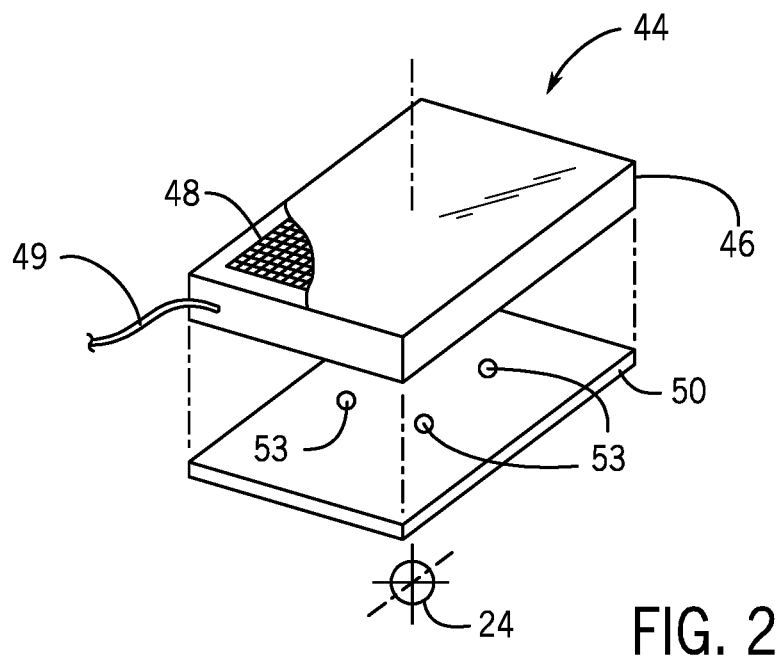
FIG. 2 is an exploded perspective view of the planar detector showing a sensor array positioned above fiducial markers and showing the location of a target region below the fiducial markers for an isocentric radiation treatment of the target region.

Referring now to FIGS. 1 and 2, the verification system of the present invention may provide for a planar image detector 44, for example, having an outer radiolucent rectangular prismatic housing 46 with a height of approximately 5 cm, a width of 33 cm, and a length of 38 cm. An upper surface of the prismatic housing 46 may be marked with indicia 45 indicating its proper orientation and the region for exposure. For example, the upper surface may be labeled with an indication that it is to be faced upward and may define a radiation exposure area as well directions of the patient left and right, head and feet. Contained within the housing 46 is a solid-state sensor array 48 providing approximately 1000×1000 sensor pixels on a pitch of 200 μm. Each pixel may provide a resolution of at least 16-bit or more than 88 dB energy range sensitivity. The sensor array 48 when positioned on the surface 30 of the patient table 28 may provide a cross-sectional image of the generally cylindrical radiation beam 20 (as collimated by a circular collimator) passing through the sensor array 48.

Planar image detectors suitable for use with the present invention are described in U.S. Pat. No. 8,218,725 hereby incorporated by reference and are commercially available from Standard Imaging of Wisconsin, USA, for example, under the tradenames QA StereoChecker, providing rows and columns of electronically readable pixels being a plurality of ionization chamber detectors, scintillation detectors, Cerenkov counters and/or solid state detectors such as semiconductor detectors, e.g. silicon, germanium or diamond counters.

The sensor array 48 may communicate by means of a cable 49 releasably attached to a computer 52. The computer 52 may be a standard "personal computer," for example, being in the form factor of a laptop providing a data receiving port (e.g., RJ-45 Ethernet) for receiving data from the sensor array 48, and an internal microprocessor communicating with a machine-readable memory storing a program that will be discussed below. The laptop may provide for a graphic display screen and keyboard of conventional design to allow for outputting or inputting of data to the program in the performance of the tasks that will be discussed.

Positioned beneath the housing 46 and affixed to the housing 46 is a water equivalent (radiolucent) plastic slab 50 having similar peripheral dimensions to the housing 46 and a height of approximately ¼ inch to hold fixed with respect to the housing 46 at least three fiducial markers 53, for example, in the form of high-density spheres embedded in the plastic slab 50 such as can be imaged (and located in three dimensions) by the x-ray beams 39 shown in FIG. 1.

Figure 3:
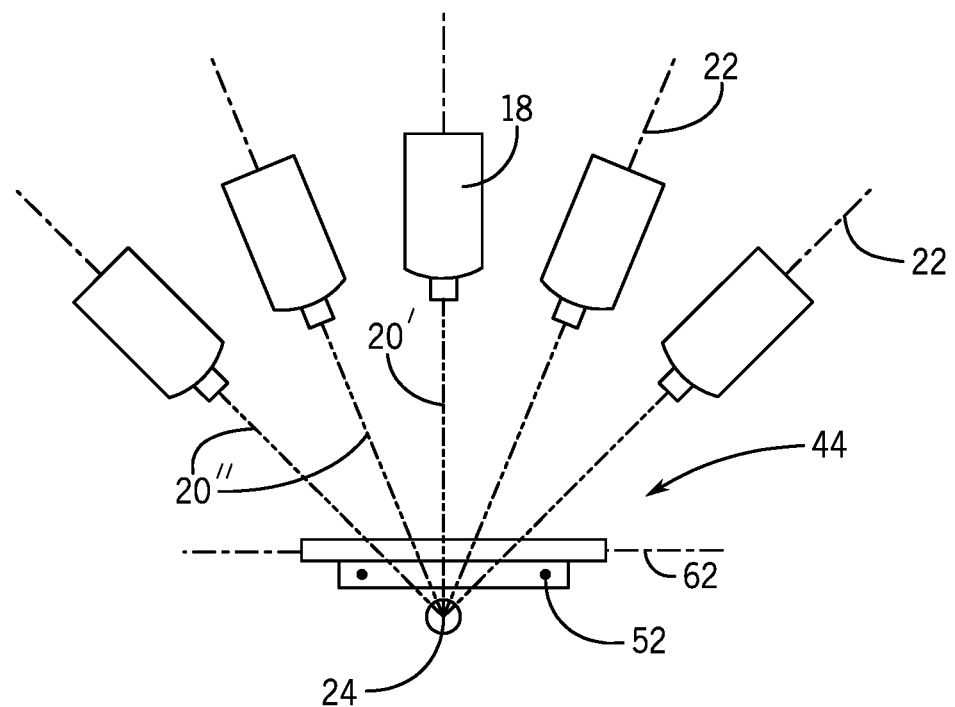
FIG. 3 is a simplified diagram showing multiple positions of the treatment head during isocentric radiation treatment about the target region position beneath the planar detector of FIGS. 1 and 2.
Figure 8:
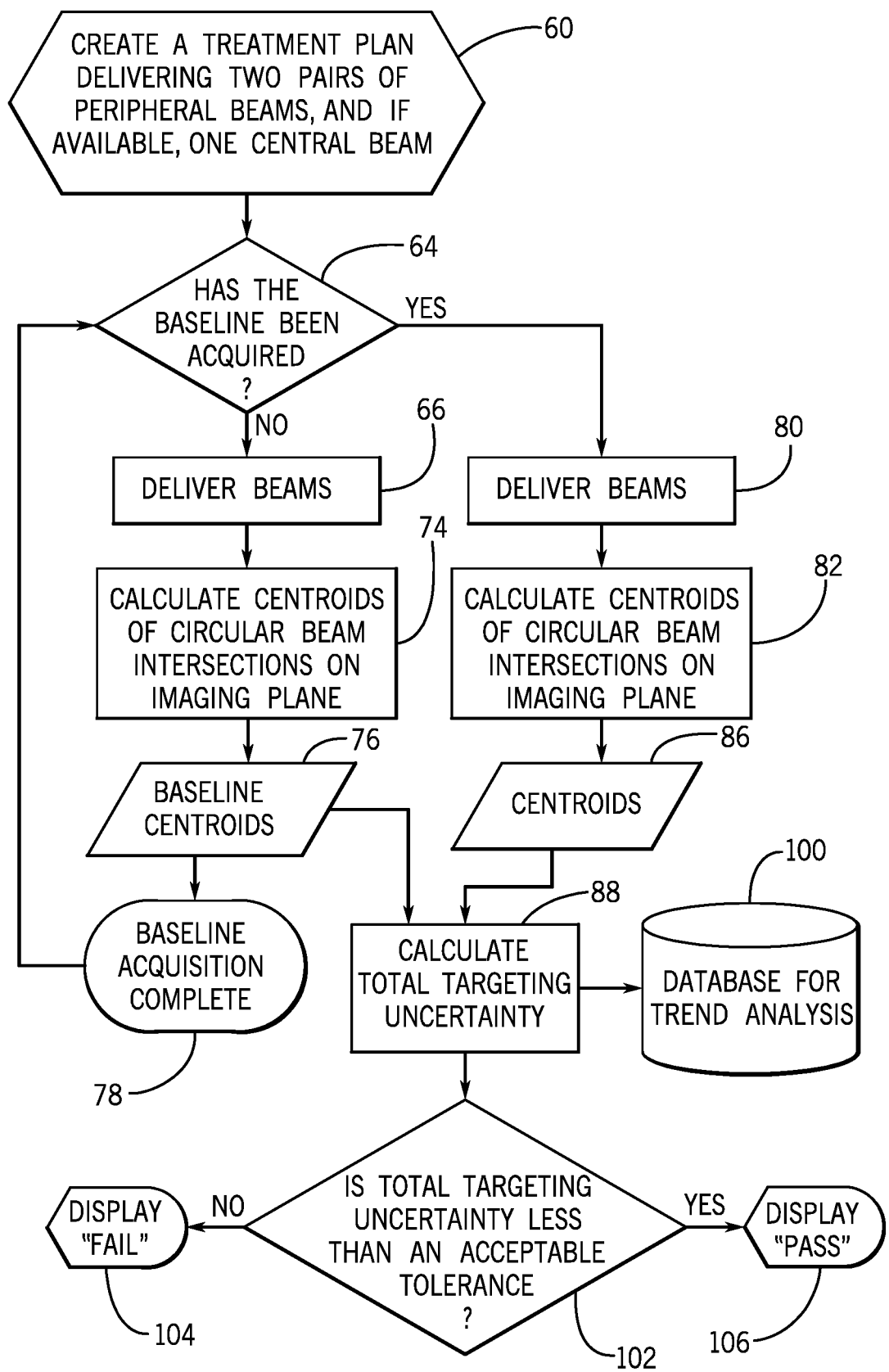
FIG. 8 is a flowchart of the program executed by the computer of FIG. 1 in implementing the verification system of the present invention.

Referring now to FIGS. 3 and 8, in a first step of the verification process, using planar image detector 44 and computer 52 per the present invention, the controller 26 may be programmed to perform a verification isocentric treatment plan delivering dose to a baseline target isocenter 24. The baseline target isocenter 24 may be defined by positional offsets between the baseline target isocenter 24 and each of the three or more fiducial markers 53 and thus may be fixed in a known location with respect to the planar image detector 44 in translation and rotation. In particular, the baseline target isocenter 24 is positioned beneath an imaging plane 62 of the planar image detector 44, where the imaging plane 62 is aligned with a plane of the sensor array 48.

The verification isocentric treatment plan will generally define a set of beams 20 and their axes 22 focused on the baseline target isocenter 24 and will also describe beam duration, collimation size, source-to-target distance and the like as is generally understood in the art and as will be automatically sequenced by the controller 26. Generally, the verification isocentric treatment plan will generate a central beam 20' with the treatment head 18 positioned in a first location with the beam 20 and axis 22 generally vertically, and at least two pairs of peripheral beams 20" at different angles from the central beam 20'. Each of these beams 20 will converge on baseline target isocenter 24 and will be exposed sequentially with movement of the treatment head 18 by the robot arm 12 therebetween.

At process block 64, if a baseline image has not been obtained, this treatment plan will be used to obtain a baseline image beginning at process block 66. At this process block 66, the x-ray sources 34 and 36 are first energized to image the fiducial markers 53 to determine a location of the fiducial markers 53 and by extension the baseline target isocenter 24. Offsets in angles of the segments 16 of the robot arm 12 with respect to the angles of the treatment plan are then adjusted by the controller 26 to provide convergence on the actual baseline target isocenter 24 and beams 20 activated in sequence.

Figure 4:
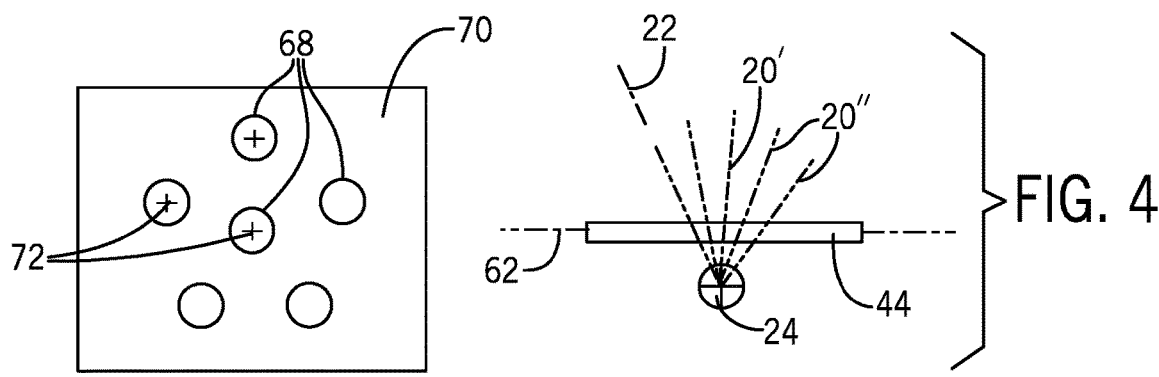
FIG. 4 is a side-by-side representation of a top plan view of the area of the planar detector showing detected areas of beam impingement and a side cross-sectional view showing central axes of the beams converging on a target region during a baseline imaging operation.

Referring also to FIG. 4, during implementation of the treatment plan at process block 66, a composite image of areas 68 of exposure in the sensor array 48 by the beam 20 passing through the sensor array 48 is acquired to produce a baseline image 70. Generally, each of the beams 20' and 20" producing this baseline image 70 as circularly collimated will produce a circular or oval-shaped exposure area 68. Ideally each of these areas 68 will be spaced from the others to be clearly distinguishable as will occur with proper positioning of the baseline target isocenter 24 below the planar image detector 44.

These areas 68 may be analyzed to find centroids 72 (for example, by an intensity-weighted, positioned-weighted averaging of each area 68 per process block 74 of FIG. 8. These baseline image centroids 72 are then stored, as indicated by process block 76, and the baseline image 70 is then complete as indicated by process block 78. This baseline image 70 is ideally obtained immediately upon factory calibration of the robotic radiation therapy system 10, for example, upon initial commissioning. Such calibration which may involve relatively complex and cumbersome techniques including physical measurement of the location of the treatment head 18 at various beam angles and the acquisition of multiple film or radiation images.

At a later verification time, after the baseline image 70 has been acquired and verification is desired, the same treatment plan used for baseline imaging per process block 60 may be recalled, and at process block 64 a verification image 71 may be obtained using this treatment plan as indicated by process block 80. Acquisition of the verification image 71 may be preceded by the process of registering the baseline target isocenter 24 to the fiducial markers 53 as described above to accommodate possible different placement of the planar image detector 44 on the patient table 28.

Although acquisition of the verification image 71 uses the same steps as used to provide the baseline image per process block 66, this treatment plan will be implemented during a later operation of the robotic radiation therapy system 10 where changes in the equipment may have affected accuracy or performance. Accordingly, in some instances, the isocenter of the beams 20 with respect to the planar image detector 44 will not coincide with the desired baseline target isocenter 24, representing an error intended to be detected during the verification procedure. For clarity and discussion, the actual isocenter of the treatment plan during this verification step will be termed verification target isocenter 92.

After the verification image 71 is obtained, its centroids 72 are calculated per process block 82 and stored per process block 86 as described above. At process block 88, the centroids 72 of the baseline image 70 are compared to the centroids 72 of the verification image 71 to deduce a number of different types of positional errors of the robotic radiation therapy system 10 as will be now discussed.

Figure 5:
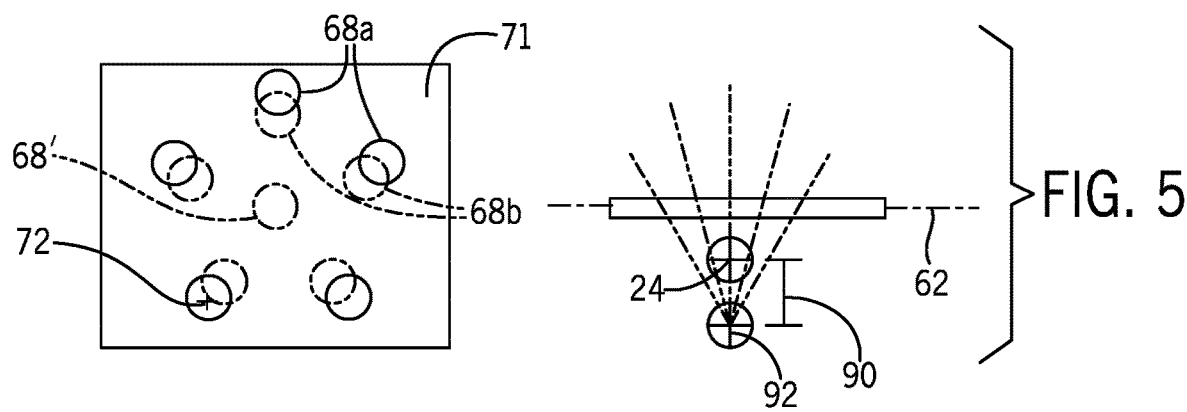
FIG. 5 is a figure similar to FIG. 4 showing a verification image produced when the verification target region is below the baseline target region where the baseline image is shown with dotted lines for comparison.

Referring now to FIG. 5 centroid of verification areas 68a may be compared to corresponding centroid of baseline areas 68b (shown with dotted lines) to detect a vertical target error 90, being a distance between the baseline target isocenter 24 and the verification target isocenter 92 of the beams 20 during the verification imaging along a direction perpendicular to the imaging plane 62. This vertical target error 90 may be deduced by radial displacement of the centroids 72 of areas 68a with respect to the centroids of area 68b about a centroid 72 of the center beam's center most area 68'. If no center most area 68' is available, the displacement may be calculated from a synthesized center point formed by an averaging of the position of the centroids 72 of all other areas 68a. The synthesis is possible by selecting a treatment plan where all beams are symmetrically angled about a central axes.

The magnitude of the radial displacement of each area 68a may be averaged together and the vertical target error 90 deduced by trigonometric calculations based on known angles of the beams 20 from vertical. Alternatively, individual radial displacements may be output or deviations between radial displacements output to identify possible errors associated with only a single beam positioning.

Generally radial expansion of the centroids of areas 68a in the verification image 71 with respect to the centroids of areas 68b of the baseline image 70 indicates a downward displacement of the verification target isocenter 92 with respect to the baseline target isocenter 24 whereas the opposite, a convergence of the centroids of areas 68a of the verification image 71 with respect to the centroids the areas 68b toward the centroid of area 68', indicates an upward displacement of the verification target isocenter 92 with respect to the baseline target isocenter 24.

Figure 6:
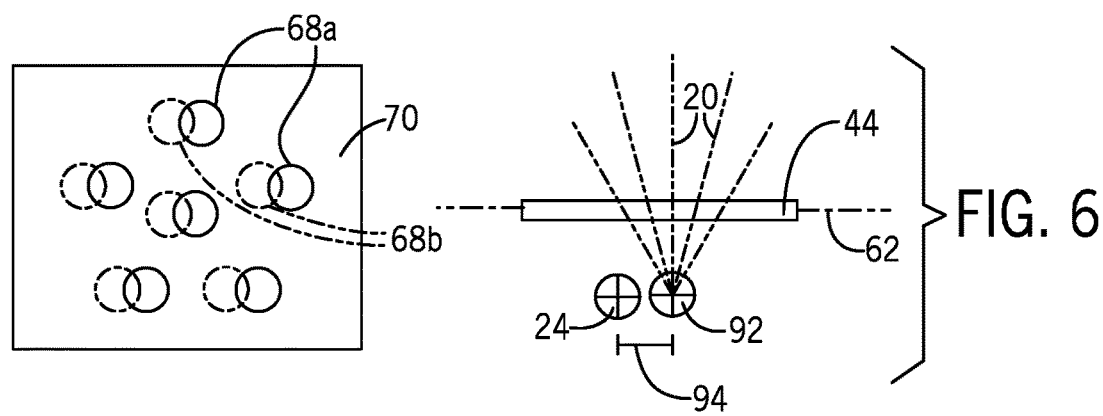
FIG. 6 is a figure similar to FIGS. 4 and 5 showing a verification image produced when the verification target region is shifted to the right of the baseline target region.

Referring now to FIG. 6, a similar technique of analysis may be used to determine a left/right or superior/inferior displacement error 94 along the imaging plane 62 between the baseline target isocenter 24 and the verification target isocenter 92. In this case, a uniform displacement of the areas 68a of the verification image 71 with respect to the corresponding areas 68b of the baseline image 70 (determined from their centroids 72) provides the amount of the displacement error 94. Depending on the direction of the displacement, both left/right and superior/inferior displacement values represented by different displacement error values 94 associated with each such displacement may be obtained.

Individual errors along each of three Cartesian coordinates may be output or analyzed, or alternatively a vector sum of the displacements along three perpendicular axes may be obtained using the technique shown in FIGS. 5 and 6 (for example, using a root mean square of the individual components) to provide a single error value. This error value may also be provided to the user, for example, directly, or after comparing the error value to an acceptable error level per process block 102 and displaying either fail indication per process block 104 or pass indication per process block 106. It will be appreciated that any of the calculated values discussed above may also be displayed directly and that pass/fail may include pass/warn/fail type displays with an intermediate step, yet still providing qualitative output.

Figure 9:
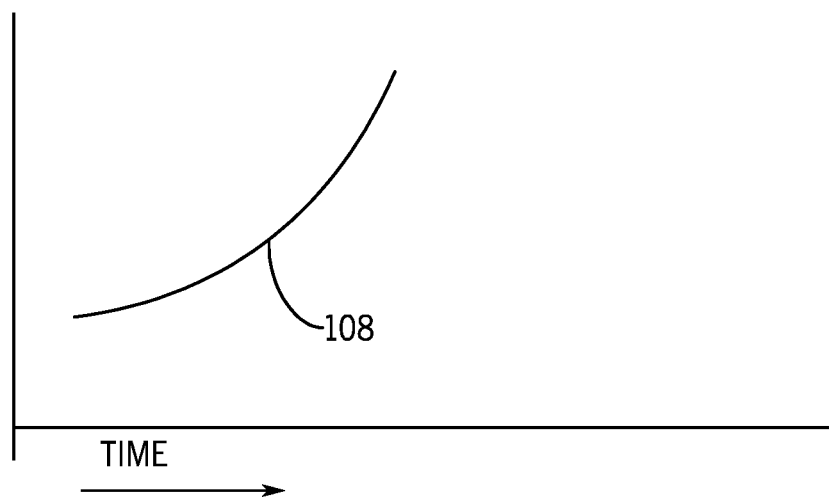
FIG. 9 is a plot of error trends that may be displayed with the present invention.

In addition, any of the measured values or error values may be stored as indicated by process block 100 of FIG. 8 together with the time and situation of measurement to provide a database for trend analysis in the shifting of the positional accuracy of the robotic radiation therapy system 10. This trend may be output, for example, as shown in FIG. 9, by means of a trendline 108 plotting a measured value on the vertical axis against time. All collected data may also be archived in a similar manner including the images 70 and 71, and values of centroids 72.

Figure 7:
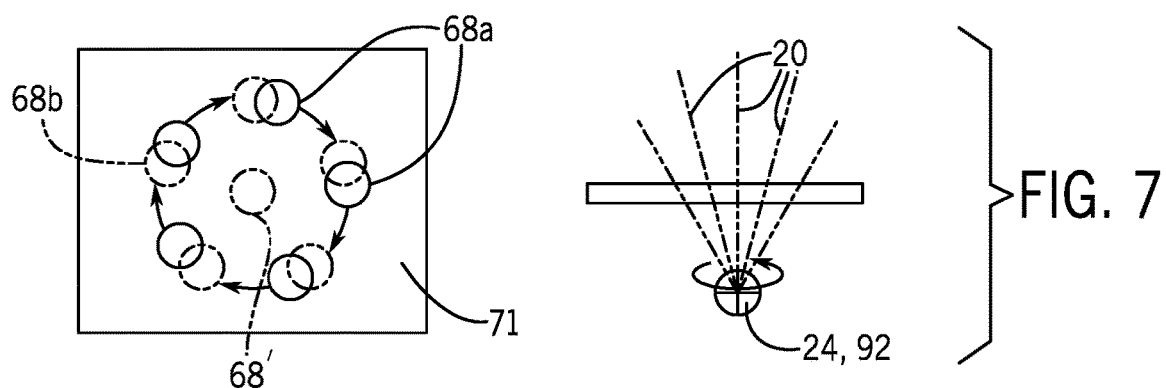
FIG. 7 is a figure similar to FIGS. 4 through 6 showing a verification image with rotation of the beams when the verification target region and baseline target region are aligned.

Referring now to FIG. 7, it will be appreciated that the invention may also be used to detect in-plane rotation, for example, about a perpendicular to the imaging plane 62. This rotation can be detected by isolating displacement components between areas 68a and 68b along a circle of constant radius about the centroid of area 68' in cases where that may prove of interest.

While a separate computer 52 is described, it will be appreciated that a properly shielded computer and display may be incorporated into the housing 46 of the planar image detector 44 according to the teachings of the present invention.

While the baseline target isocenter 24 is preferably beneath the imaging plane 62, it will be appreciated that a similar effect may be obtained with displacements above the imaging plane 62. In addition other collimation forms may be acceptable with proper calibration.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a processor" and "a computer" or can be understood to include one or more processors or computers that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

What we claim is:

1. A radiotherapy verification system for use with a robotic radiotherapy machine providing a treatment head emitting a beam of collimated high-energy radiation and maneuverable by a multi-axis robot arm about a patient support, the radiotherapy verification system comprising:
    a planar imaging device adapted to detect areas of high-energy radiation passing through a plane of the planar imaging device; and
    an electronic computer communicating with the planar imaging device when the planar imaging device is supported by the patient support at a support location fixed relative to the patient support with movement of the patient support and/or the treatment head during operation of the robotic radiotherapy machine to implement an isocentric treatment plan, the electronic computer executing a stored program held in non-transitory computer readable medium to operate:
    (a) in a first mode recording first location information for the areas during a first execution of the isocentric treatment plan by the robotic radiotherapy machine to provide baseline location information, the isocentric treatment plan directed to a target region displaced from the plane of the planar imaging device, and the planar imaging device fixed at the support location; and
    (b) in a second mode recording second location information for the areas during execution of a second execution of the isocentric treatment plan with the planar imaging device fixed at the support location to provide verification location information and comparing the verification location information to the baseline location information to indicate displacement of the target region between the first execution and second execution.

2. The radiotherapy verification system of claim 1 wherein the second mode further determines centroids of areas and compares the verification location information to the baseline location information to compare centroids of the areas.

3. The radiotherapy verification system of claim 1 wherein the displacement of the target region indicates displacement in three mutually perpendicular directions including displacement above or below the plane of the imaging device.

4. The radiotherapy verification system of claim 1 wherein the indication of displacement provides a distance value equal to the displacement of the target region between the first execution and second execution.

5. The radiotherapy verification system of claim 4 wherein the indication provides a pass/fail type output determined by comparing a distance value equal to the displacement of the target region between the first execution and second execution to a predetermined threshold value.

6. The radiotherapy verification system of claim 1 wherein the planar imaging device further includes a set of radiopaque fiducial markers affixed at a predetermined location with respect to the planar imaging device.

7. The radiotherapy verification system of claim 1 wherein the electronic computer further operates in the second mode to compare the verification location information to the baseline location information to indicate a rotation of the areas between the first execution and second execution.

8. The radiotherapy verification system of claim 1 wherein the electronic computer is separable from the planar imaging device and connected by a releasable electronic cable.

9. The radiotherapy verification system of claim 1 wherein indication is output by the electronic computer on a display screen.

10. The radiotherapy verification system of claim 1 wherein the first and second location information received by the electronic computer comprises intensity values associated with pixels identified to locations within the plane of the imaging device.

11. The radiotherapy verification system of claim 1 wherein a number of areas is at least four.

12. The radiotherapy verification system of claim 1 wherein the treatment head provides a beam having radial symmetry.

13. A radiotherapy verification system for use with a robotic radiotherapy machine providing a treatment head emitting a beam of collimated high-energy radiation and maneuverable by a multi-axis robot arm, the radiotherapy verification system comprising:
    a planar imaging device adapted to detect areas of high-energy radiation passing through a plane of the planar imaging device; and
    an electronic computer communicating with the planar imaging device to receive first location information about the areas and executing a stored program held in non-transitory computer readable medium to operate:
    (a) in a first mode recording first location information for the areas during a first execution of an isocentric treatment plan by the robotic radiotherapy machine to provide baseline location information, the isocentric treatment plan directed to a target region displaced from the plane of the planar imaging device; and
    (b) in a second mode recording second location information for the areas during execution of a second execution of the isocentric treatment plan to provide verification location information and comparing the verification location information to the baseline location information to indicate displacement of the target region between the first execution and second execution;

wherein the planar imaging device further includes a set of radiopaque fiducial markers affixed at a predetermined location with respect to the planar imaging device; and wherein the planar imaging device has an upper surface positionable toward the treatment head and radiopaque fiducial markers are positioned beneath the upper surface of a radiation sensor of the planar imaging device to block a portion of radiation received by the radiation sensor of the planar imaging device.

14. The radiotherapy verification system of claim 13 wherein the upper surface is marked to indicate its proper orientation during use.

15. A radiotherapy verification system for use with a robotic radiotherapy machine providing a treatment head emitting a beam of collimated high-energy radiation and maneuverable by a multi-axis robot arm, the radiotherapy verification system comprising:
   a planar imaging device adapted to detect areas of high-energy radiation passing through a plane of the planar imaging device; and
   an electronic computer communicating with the planar imaging device to receive location information about the areas and executing a stored program held in non-transitory computer readable medium to operate:
   (a) in a first mode recording first location information for the areas during a first execution of an isocentric treatment plan by the robotic radiotherapy machine to provide baseline location information, the isocentric treatment plan directed to a target region displaced from the plane of the planar imaging device; and
   (b) in a second mode recording second location information for the areas during execution of a second execution of the isocentric treatment plan to provide verification location information and comparing the verification location information to the baseline location information to indicate displacement of the target region between the first execution and second execution; and
   wherein the electronic computer further records the location information for the areas in multiple operations in the second mode finked to time to provide for a history of indications to provide trend information.

16. The radiotherapy verification system of claim 15 wherein the trend information is displayed as a plot indicating a measure related to displacement of the target region between the first execution and second execution as a function of time.

17. A method of verifying operation of a robotic radiotherapy machine providing a treatment head emitting a beam of collimated high-energy radiation and maneuverable by a multi-axis robot arm about a patient support, employing a radiotherapy verification system having:
   a planar imaging device adapted to detect areas of high-energy radiation passing through a plane of the planar imaging device; and
   an electronic computer communicating with the planar imaging device when the planar imaging device is supported by the patient support at a support location fixed relative to the patient support with movement of the patient support and/or the treatment head during operation of the robotic radiotherapy machine to implement an isocentric treatment plan, the electronic computer executing a stored program held in non-transitory computer readable medium to operate:
   in a first mode recording first location information for the areas during a first execution of isocentric treatment plan by the robotic radiotherapy machine to provide baseline location information, the isocentric treatment plan directed to a target region displaced from the plane of the planar imaging device, and the planar imaging device fixed at the support location; and
   in a second mode recording second location information for the areas during execution of a second execution of the isocentric treatment plan with the planar imaging device fixed at the support location to provide verification location information and comparing the verification location information to the baseline location information to indicate displacement of the target region between the first execution and second execution;
   the method comprising the steps of:
   (a) operating the radiotherapy verification system to collect baseline location information;
   (b) operating the radiotherapy system to collect verification information and to output to a user an indication of displacement of the target region between step (a) and step (b).

18. The method of claim 17 further including the step of applying circular collimation to the high-energy radiation beam before steps (a) and (b).

19. The method of claim 17 wherein the planar imaging device further includes set of radiopaque fiducial markers affixed at predetermined locations with respect to the planar imaging device including the step of calibrating the robotic radiotherapy machine by entering the locations of the fiducial markers with respect to a desired target region of the treatment plan wherein that desired target region is displaced from the plane of the planar imaging device.

* * * * *